US00RE45344E

(19) United States
(12) Reissued Patent
Nanjo

(10) Patent Number: US RE45,344 E
(45) Date of Reissued Patent: Jan. 20, 2015

(54) RETINAL FUNCTION MEASUREMENT APPARATUS

(75) Inventor: Tsuguo Nanjo, Toyohashi (JP)

(73) Assignee: Nidek Co., Ltd., Gamagori (JP)

(21) Appl. No.: 13/554,180

(22) Filed: Jul. 20, 2012

Related U.S. Patent Documents

Reissue of:
(64) Patent No.: 7,506,978
Issued: Mar. 24, 2009
Appl. No.: 11/702,608
Filed: Feb. 6, 2007

U.S. Applications:
(62) Division of application No. 13/071,163, filed on Mar. 24, 2011, now Pat. No. Re. 44,226, which is an application for the reissue of Pat. No. 7,506,978.

(30) Foreign Application Priority Data

Feb. 6, 2006 (JP) ..... 2006-28303

(51) Int. Cl.
*A61B 3/10* (2006.01)
*A61B 3/14* (2006.01)

(52) U.S. Cl.
USPC ..... 351/204; 351/206; 351/208

(58) Field of Classification Search
USPC ..... 359/204, 208
See application file for complete search history.

(56) References Cited

U.S. PATENT DOCUMENTS

| | | | | |
|---|---|---|---|---|
| 5,537,162 | A | 7/1996 | Hellmuth et al. | |
| 5,847,806 | A | 12/1998 | Mihashi | |
| 6,377,349 | B1 | 4/2002 | Fercher | |
| 6,478,424 | B1 | 11/2002 | Grinvald et al. | |
| 2005/0203422 | A1 * | 9/2005 | Wei | 600/476 |
| 2006/0066869 | A1 | 3/2006 | Ueno et al. | |

FOREIGN PATENT DOCUMENTS

| | | |
|---|---|---|
| JP | A-10-0033484 | 2/1998 |
| JP | A 11-325849 | 11/1999 |
| JP | A-11-325849 | 11/1999 |
| JP | A-2002-521115 | 7/2002 |
| JP | A-2004-028970 | 1/2004 |
| JP | A-2004-037391 | 2/2004 |
| WO | WO 00/06015 | 2/2000 |

OTHER PUBLICATIONS

Aug. 6, 2008 Office Action issued in U.S. Appl. No. 11/702,608.
Dec. 2, 2008 Notice of Allowance issued in U.S. Appl. No. 11/702,608.
Feb. 24, 2012 Office Action issued in U.S. Appl. No. 13/071,163.

* cited by examiner

*Primary Examiner* — James Jones
(74) *Attorney, Agent, or Firm* — Oliff PLC

(57) ABSTRACT

A retinal function measurement apparatus capable of measuring a retinal function accurately and precisely. The apparatus has a first image obtaining optical system for obtaining a tomographic image of a fundus by optical coherence tomography using low coherent light, the optical system including a light source emitting the low coherent light, a scanning unit scanning measurement light being a part of the emitted low coherent light on the fundus, an interference optical system for synthesizing the measurement light reflected from the fundus and reference light being a part of the emitted low coherent light to interfere, and a first photodetector photoreceiving the interfered light, a stimulating light irradiation optical system for performing irradiation of stimulating light onto the fundus, and an image processing unit obtaining information on a retinal function by performing processing on a first tomographic image and a second tomographic image before/after the irradiation of the stimulating light.

2 Claims, 4 Drawing Sheets

RETINAL FUNCTION MEASUREMENT APPARATUS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*More than one reissue application has been filed for the reissue of U.S. Pat. No. 7,506,978 filed Feb. 6, 2007 and issued Mar. 24, 2009. The reissue applications are Ser. No. 13/554,180 filed Jul. 20, 2012 and Ser. No. 13/071,163 filed Mar. 24, 2011. This Application is a Divisional and Reissue application Ser. No. 13/071,163 filed Mar. 24, 2011 U.S. Pat. No. Re. 44,226, which is a Reissue of U.S. Pat. No. 7,506,978 filed Feb. 6, 2007 and issued on Mar. 24, 2009.*

BACKGROUND OF THE INVENTION

1. Field of the Invention

The present invention relates to an apparatus which measures a retinal function by photographing a fundus.

2. Description of Related Art

There is known an apparatus (system) which noninvasively performs imaging of a retinal function (see International Publication No. WO 00/06015 (Japanese Patent Application Unexamined Publication No. 2002-521115)). The apparatus includes an imaging illumination device which illuminates a retina, a stimulating illumination device which guides a functional response of the retina, and an imaging device which photo-receives light from the retina via an imaging optical system, measures the retinal function based on states of retinal images before/after irradiation of stimulating light onto the retina, and performs imaging of a result of the measurement for evaluation.

Such an apparatus reads a change of brightness of the retinal image after the irradiation of the stimulating light with respect to brightness of the retinal image before the irradiation of the simulating light; however, since a change of the retina (a change of an activity of nervous tissue) by the stimulating light is minute, it is important to detect the change accurately. In addition, in order to perform more precise measurement of the retinal function, it is necessary to perform the measurement over a depth direction of the retina.

SUMMARY OF THE INVENTION

An object of the invention is to overcome the problems described above and to provide a retinal function measurement apparatus capable of measuring a retinal function accurately and precisely.

To achieve the objects and in accordance with the purpose of the present invention, a retinal function measurement apparatus has a first image obtaining optical system for obtaining a tomographic image of a fundus by optical coherence tomography using low coherent light, the first image obtaining optical system including a light source which emits the low coherent light, a scanning unit which scans measurement light being a part of the emitted low coherent light on the fundus, an interference optical system for synthesizing the measurement light reflected from the fundus and reference light being a part of the emitted low coherent light to interfere, and a first photodetector which photo-receives the interfered light, a stimulating light irradiation optical system for performing irradiation of stimulating light onto the fundus, and an image processing unit which obtains information on a retinal function by performing processing on a first tomographic image before the irradiation of the stimulating light and a second tomographic image after the irradiation of the stimulating light.

Additional objects and advantages of the invention are set forth in the description which follows, are obvious from the description, or may be learned by practicing the invention. The objects and advantages of the invention may be realized and attained by the apparatus in the claims.

BRIEF DESCRIPTION OF THE DRAWINGS

The accompanying drawings, which are incorporated in and constitute apart of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
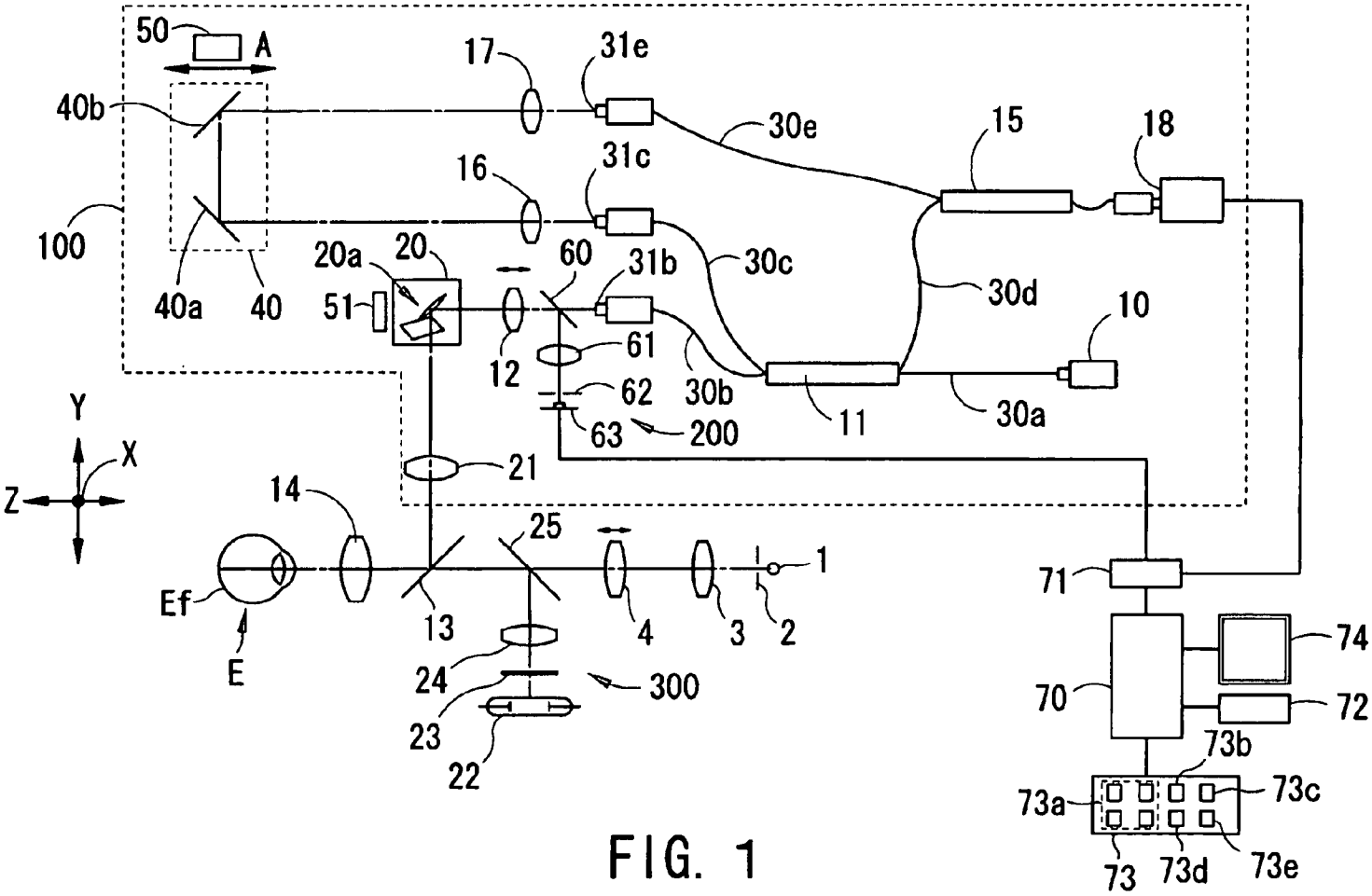
FIG. 1 is a view showing a schematic configuration of an optical system and a control system of a retinal function measurement apparatus consistent with one preferred embodiment of the present invention.

A detailed description of one preferred embodiment of a retinal function measurement apparatus embodied by the present invention is provided below with reference to the accompanying drawings. FIG. 1 is a view showing a schematic configuration of an optical system and a control system of a retinal function measurement apparatus consistent with one preferred embodiment of the present invention. In the preferred embodiment, a depth direction of an examinee's eye is referred to as a Z-direction, a horizontal direction orthogonal to the depth direction is referred to as an X-direction, and a vertical direction orthogonal to the depth direction is referred to as a Y-direction.

The optical system of the present apparatus includes an optical coherence tomography (OCT) optical system 100 for obtaining an infrared (monochrome) tomographic (sectional) image of a fundus Ef of an examinee's eye E, a scanning laser ophthalmoscope (SLO) optical system 200 for obtaining an infrared (monochrome) front (surface) image of the fundus Ef, and a stimulating light irradiation optical system 300 for performing irradiation of stimulating light for stimulating a retina onto the fundus Ef.

A description will be given to the OCT optical system 100. An infrared light source 10 for measurement (photographing) such as a super luminescent diode (SLD) is a light source which emits low coherent light used as measurement light (photographing light, object light) and reference light, for example, a light source having a band of 50 nm with a center wavelength of 840 nm (a range with wavelengths of 815 to 865 nm). Infrared light from the light source 10 passes through an optical fiber 30a being a light guide, and enters a fiber coupler 11 to be divided into the measurement light and the reference light.

On an optical path of the measurement light from the fiber coupler 11 to the fundus Ef, arranged are an optical fiber 30b being a light guide, a relay lens 12 movable in a direction of an optical axis in accordance with refractive power of the eye E, a scanning unit 20, a relay lens 21, a dichroic mirror 13, and an objective lens 14. In addition, on an optical path of the measurement light from the fundus Ef to a photodetector 18, arranged are the objective lens 14 to the fiber coupler 11, an optical fiber 30d being a light guide, and a fiber coupler 15. An end 31b of the optical fiber 30b is arranged in a position conjugate with the fundus Ef. The scanning unit 20 includes a pair of galvano mirrors 20a, which are made swingable (rotatable) by a driving mechanism part 51 to scan the measurement light in the X- and/or Y-directions. In addition, reflective surfaces of the galvano mirrors 20a are arranged in positions conjugate with a pupil of the eye E (in the preferred embodiment, arranged to have a conjugate positional relationship between an intermediate position of the galvano mirrors 20a and the pupil). The dichroic mirror 13 has properties of reflecting the light from the light source 10 and transmitting the other light (light from a light source 1, light from a light source 22 (a filter 23)). The dichroic mirror 13 makes an optical axis of the OCT optical system 100 and the SLO optical system 200, and an optical axis of the stimulating light irradiation optical system 300 coaxial.

The measurement light exiting from the fiber end 31b passes through the relay lens 12, is reflected by the galvano mirrors 20a, passes through the relay lens 21, is reflected by the dichroic mirror 13, passes through the objective lens 14, and converges at the fundus Ef. The measurement light reflected from the fundus Ef enters the fiber end 31b via the objective lens 14 to the relay lens 12, passes through the optical fiber 30b, the fiber coupler 11 and the optical fiber 30d, and enters the fiber coupler 15.

On the other hand, on an optical path of the reference light from the fiber coupler 11 to the photodetector 18, arranged are an optical fiber 30c being a light guide, a collimator lens 16, an optical path length changing unit 40, a condenser lens 17, an optical fiber 30e being a light guide, and the fiber coupler 15. The optical path length changing unit 40 includes total reflection mirrors 40a and 40b, and is movable in the direction of the optical axis (in a direction of an arrow A) by a driving mechanism part 50 to change an optical path length of the reference light.

The reference light exiting from an end 31c of the optical fiber 30c passes through the collimator lens 16, is reflected by the total reflection mirrors 40a and 40b, passes through the condenser lens 17, enters an end 31e of the optical fiber 30e, passes through the optical fiber 30e, and enters the fiber coupler 15.

The measurement light and the reference light entering the fiber coupler 15 are synthesized to be photo-received on (detected by) the photodetector 18, and based on an interference phenomenon when an optical path length of the measurement light reflected by layers of the fundus Ef is equal to the optical path length of the reference light changed by the optical path length changing unit 40, intensity distribution of the reflected measurement light in the Z-direction is obtained (in the preferred embodiment, this method is referred to as an A-scan (linear scanning). In addition, by scanning of the measurement light in the X- or Y-direction and the change of the optical path length of the reference light, a two-dimensional tomographic image in an X-Z plane or a Y-Z plane of the fundus Ef is obtained (in the preferred embodiment, this method is referred to as a B-scan (longitudinal scanning)). In addition, by the scanning of the measurement light in the X- and Y-directions, a two-dimensional tomographic image in an X-Y plane of the fundus Ef is obtained (in the preferred embodiment, this method is referred to as a C-scan (transversal scanning)). Further, by making use of these methods, a three-dimensional tomographic image of the fundus Ef is obtained. In other words, by the scanning of the measurement light in the X- and Y-directions and the change of the optical path length of the reference light, the three-dimensional tomographic image of the fundus Ef is obtained.

Incidentally, in the A-scan, a position (a portion) where high intensity is first obtained is a surface (surface layer) of the fundus Ef. Accordingly, a surface (a surface layer) image of the fundus Ef is obtained by connecting positions (portions) where high intensity is first obtained in the A-scan with the scanning of the measurement light in the X- and Y-directions.

In addition, since the tomographic image obtained by the B-scan is constituted by a one-axis scan of an A-scan signal, it is possible to accurately detect the position of the tomographic image on the surface image by comparing an image signal of a part of the surface image and an image signal of a surface part of the tomographic image.

The SLO optical system 200 will be described. The SLO optical system 200 in the preferred embodiment shares the light source 10, the optical fibers 30a and 30b, the scanning unit 20, the dichroic mirror 13, the objective lens 14, and the like with the OCT optical system 100. In addition, a half mirror (a beam splitter) 60 is arranged between the fiber end 31b and the relay lens 12, and on a reflection side (direction) of the half mirror 60, arranged are a condenser lens 61 and an aperture 62 configurating a confocal optical system, and a photodetector 63. The aperture 62 is arranged in a position conjugate with the fundus Ef. According to such a configuration, the infrared measurement light from the light source 10 is scanned in the X- and Y-directions by the scanning unit 20, and the reflection measurement light from a position (a portion) of the fundus Ef conjugate with the aperture 62 is photo-received on the photodetector 63 to obtain a front image of the fundus Ef.

A description will be given to the stimulating light irradiation optical system 300. The stimulating light irradiation optical system 300 includes the light source 22 such as a flash light, the wavelength selecting filter 23, a projection lens 24, a half mirror 25, and the objective lens 14. The wavelength selecting filter 23 has a property of selectively transmitting a visible wavelength capable of stimulating the retina. The wavelength selecting filter 23 may be arranged such that replacement of (selection among) a plurality of wavelength selecting filters such as a filter for stimulating a cone, a filter for stimulating a rod, a color filter which transmits only red, green or blue is made as appropriate.

The light source 22 is arranged in a position conjugate with the vicinity of the pupil of the eye E via the projection lens 24 and the objective lens 14. Light (stimulating light) emitted from the light source 22 passes through the wavelength selecting filter 23 and the projection lens 24, is reflected by the half mirror 25, passes through the dichroic mirror 13 and the objective lens 14, is once converged in the vicinity of the pupil of the eye E, and then illuminates the fundus Ef uniformly.

A fixation target presenting optical system includes the visible light source 1 for fixation such as a light emitting diode (LED), a diaphragm 2, a collimator lens 3, a relay lens 4, and the objective lens 14. The diaphragm 2 is arranged in a position conjugate with the fundus Ef via the collimator lens 3, the relay lens 4 and the objective lens 14.

A calculation control part 70 including a CPU which performs control of the whole apparatus and the like, is connected with the light sources 1, 10 and 22, the driving mechanism part 50, the driving mechanism part 51, the photodetectors 18 and 63, an image processing part 71, a memory part 72, an operation part 73 provided with various switches and the like, and a monitor (a display part) 74. Based on photo-receiving signals from the photodetector 63 and the photodetector 18, and the like, the image processing part 71 performs formation of the front image of the fundus Ef, formation of the tomographic image of the fundus Ef, formation of information on the retinal function (imaging of the retinal function and the like), and the like. In addition, the front image, the tomographic image, the information on the retinal function and the like which are formed by the image processing part 71, are displayed on the monitor 74. The operation part 73 is provided with an image obtaining condition setting switch group 73a, an image obtaining switch 73b, a stimulating light irradiation switch 73c, a retinal function analyzing switch 73d, a tomographic image obtaining position setting switch 73e, and the like. By operating the switch group 73a, selection of the image to be obtained among the two-dimensional tomographic image of the X-Z plane or the Y-Z plane by the B-scan, the two-dimensional tomographic image in the X-Y plane by the C-scan, and the three-dimensional tomographic image, setting of intervals of image obtaining in the Z-direction, and the like are performed.

An operation of the apparatus having the above-mentioned configuration will be described. Here, described is a method of measuring the retinal function when the two-dimensional tomographic images in the X-Y plane by the C-scan (hereinafter, also referred to as a C-scan image) are obtained at a plurality of different positions in the Z-direction as the tomographic image. First, conditions for obtaining the C-scan images, the intervals of the image obtaining in the Z-direction, and the like are set by the switch group 73a.

Figure 2:
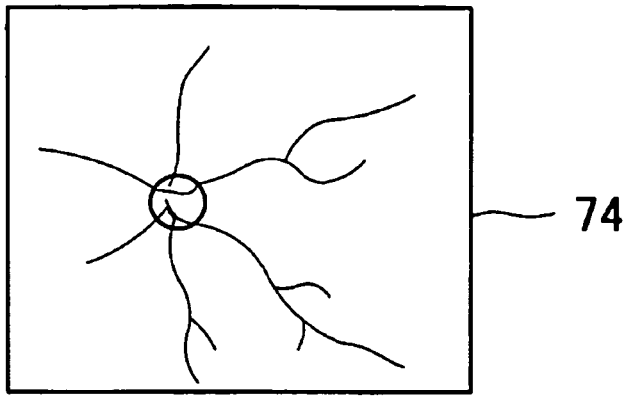
FIG. 2 is a view showing an example of a fundus front image for observation displayed on a monitor.

The measurement light from the light source 10 is scanned two-dimensionally on the fundus Ef via the OCT optical system 100, and the measurement light reflected from the fundus Ef is photo-received on the photodetector 63 via the SLO optical system 200. Based on the photo-receiving signal from the photodetector 63, the image processing part 71 makes the monitor 74 display the front image of the fundus Ef in real time (see FIG. 2). In addition, based on the front image for observation displayed on the monitor 74, focusing is obtained on the fundus Ef, and the eye E is fixed by lighting the light source 1 for fixation.

When alignment between the eye E and the apparatus is completed, the tomographic image before the irradiation of the stimulating light is obtained (photographed). When the switch 73b is pressed, the calculation control part 70 controls to drive the driving mechanism parts 50 and 51 to move the optical path length changing unit 40 in the direction of the optical axis in response to the driving of the scanning unit 20 so as to obtain the tomographic images at the set intervals of the image obtaining. The photodetector 18 sequentially detects interference light obtained by synthesizing the measurement light reflected by the fundus Ef and the reference light, and the image processing part 71 obtains intensity distribution of the reflection measurement light in the X- and Y-directions. By moving the optical path length changing unit 40 in the direction of the optical axis, intensity distribution of the reflection measurement light in the Z-direction at every set interval is obtained. Then, the image processing part 71 obtains the two-dimensional tomographic images (C-scan images) of the fundus Ef based on the obtained intensity distribution of the reflection measurement light in the X- and Z-directions at every set depth position (set positions in the Z-direction). In addition, the image processing part 71 obtains the front image of the fundus Ef at the same time, and associates the tomographic images and the front image to store them in the memory part 72.

Next, the tomographic image after the irradiation of the stimulating light is obtained (photographed). When the switch 73c is pressed, the calculation control part 70 lights the light source 22 to irradiate the stimulating light onto the fundus Ef. Accordingly, cells composing the retina are stimulated to bring about a change in an activity of nerve cells.

After the irradiation of the stimulating light, the calculation control part 70 obtains the two-dimensional tomographic images (C-scan images) and the front image of the fundus Ef after the irradiation of the stimulating light by the OCT optical system 100, the SLO optical system 200 and the image processing part 71 to store them in the memory part 72. The obtainment of the images after the irradiation of the stimulating light may be performed with time at predetermined intervals (e.g. one second, two seconds, and forth after the irradiation of the stimulating light), not one time, so as to know the change of the retinal function. In addition, in the preferred embodiment, operations from the irradiation of the stimulating light to the obtainment of the images after the irradiation are performed automatically; however, the present invention is not limited thereto, and the respective operations may be performed manually.

When the images before/after the irradiation of the stimulating light are stored in the memory part 72 and the switch 73d is pressed, the image processing part 71, based on the tomographic images before/after the irradiation of the stimulating light stored in the memory part 72, measures the retinal function according to a difference of brightness (luminance) between the tomographic images to display a result of the measurement on the monitor 74. When the cells composing the retina are stimulated by the irradiation of the stimulating light onto the fundus Ef, the change in activity of the nerve cells occurs, and a change in intensity (reflectance) of the measurement light reflected by the irradiated part also occurs. Therefore, by reading a change in brightness (luminance) of the tomographic images before/after the irradiation of the stimulating light, a change of an endogenous signal caused by the change in activity of the nerve cells can be obtained, and thereby the retinal function can be measured.

Figure 3:
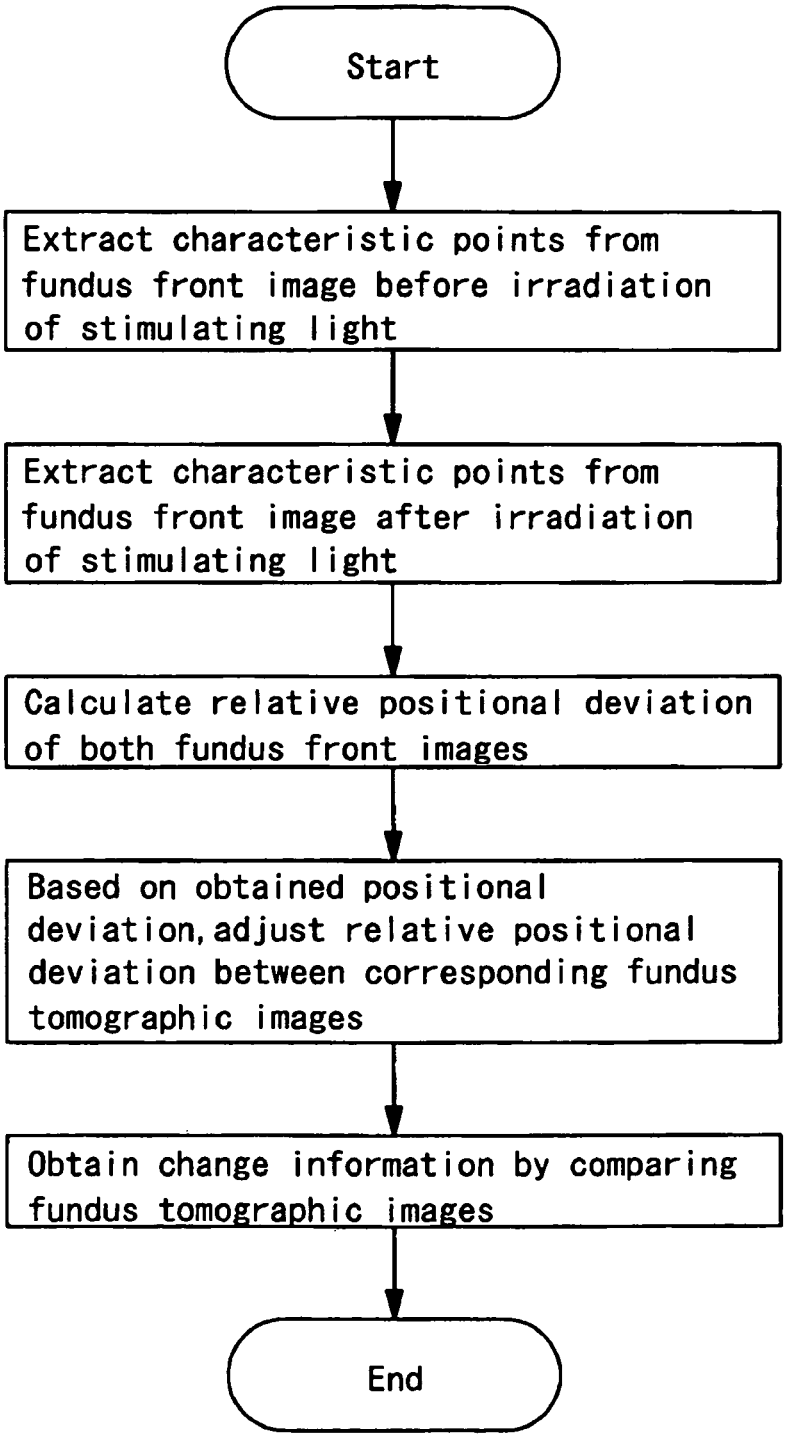
FIG. 3 is a flowchart for showing a method of comparing a fundus tomographic image before irradiation of stimulating light and a fundus tomographic image after the irradiation of the stimulating light.

Next, a method of measuring the retinal function will be described with reference to FIG. 3.

In measuring the retinal function, the image processing part 71 performs positional adjustment of the front images before/after the irradiation of the stimulating light stored in the memory part 72. For the positional adjustment, characteristic points such as a blood vessel, an optic disc and a macula, are extracted from the front images before/after the irradiation of the stimulating light by image processing, and a position where the characteristic points of the front images match the most is calculated by calculating processing. The method of the positional adjustment is not limited thereto, and a known image processing technique may be employed.

When relative positional deviation between the front images before/after the irradiation of the stimulating light is obtained by the positional adjustment, the image processing part 71 performs calculating processing so as to cancel out relative positional deviation between the tomographic images stored in association with the front images based on the obtained positional deviation. The image processing part 71 calculates the change in brightness of the tomographic image after the irradiation of the stimulating light with respect to the tomographic image before the irradiation of the stimulating light for every pixel in a state where the positional deviation between the tomographic images before/after the irradiation of the stimulating light is cancelled out (corrected). The image processing part 71 makes obtained information on the change in brightness corresponded to each pixel and displayed on the monitor 74. A method of displaying the information on the change in brightness includes a method of displaying the information as a light and shade image, a method of displaying the information as numeric values such as a difference and a ratio, and a method of displaying the information in the form of a diagram by performing calculating processing on numeric values by a predetermined analysis program for evaluating the retinal function. The tomographic images which are compared for measuring the retinal function are both obtained at the same depth position (in the same position in the Z-direction). Accordingly, in the preferred embodiment, regarding the tomographic images obtained at every set interval in the Z-direction, the information on the change in brightness thereof before/after the irradiation of the stimulating light is displayed on the monitor 74, thereby the change of the retinal function in the depth direction of the fundus Ef can be measured in detail. In addition, the tomographic images in a predetermined position in the Z-direction may be compared, instead of comparing all the obtained tomographic images.

The tomographic image is suited for the measurement of the retinal function because a resolution in the depth direction (Z-direction) is excellent; however, not suited for the correction of the positional deviation because a resolution in an intersection direction (X- and Y-directions) is not favorable and the characteristic points are hard to extract. The front image is suited for the correction of the positional deviation because a resolution in the intersection direction is excellent and the characteristic points are easy to extract.

Next, a description will be given to a method of measuring the retinal function by obtaining the two-dimensional tomographic image in the X-Z plane or the Y-Z plane by the B-scan (hereinafter, referred to as a B-scan image) as the tomographic image.

Figure 4:
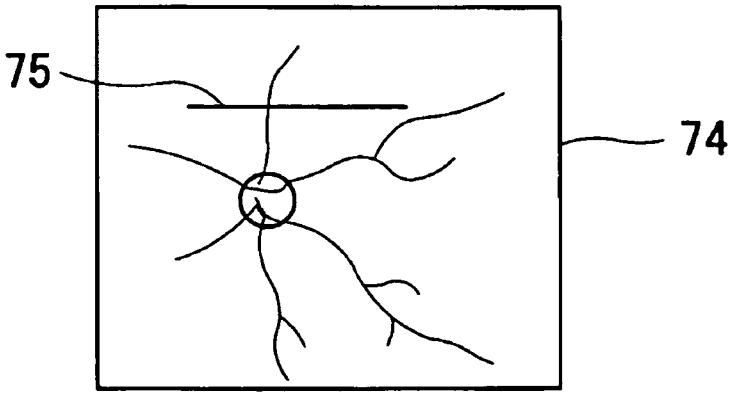
FIG. 4 is a view showing an example of positional information for obtaining the fundus tomographic image, which is set on the fundus front image for observation.

First, conditions for obtaining the B-scan image are set by the switch group 73a. In addition, a position for obtaining the B-scan image is set based on the front image for observation displayed on the monitor 74. A line 75 indicating the image obtaining position (a measurement position) which is electronically displayed on the front image displayed on the monitor 74 (see FIG. 4) is moved by the switch 73e. In the preferred embodiment, the line 75 has a straight form; however, it is possible to set the line 75 to have an arbitrary form, for example, the line 75 may have a curved form.

When the image obtaining position is set, the image processing part 71 makes the memory part 72 store information on a display position of the line 75 with respect to the front image displayed on the monitor 74. The information on the display position of the line 75 with respect to the front image is obtained, for example, as information on a position of the line 75 with respect to the characteristic points of the front image.

Next, when the switch 74b is pressed, the calculation control part 70 controls the memory part 72 to store the front image displayed on the monitor 74, and controls to drive the scanning unit 20 to scan the measurement light, based on the display position of the line 75 set on the front image, so as to obtain the tomographic image in that position. Since a relationship between the display position of the line 75 (the position on the monitor) and a scanning position of the measurement light by the scanning unit 20 is determined in advance, the calculation control part 70 controls the driving mechanism part 51 to scan the measurement light with respect to the scanning position and a scanning range corresponding to the set display position and a length of the line 75. In addition, the calculation control part 70 controls the driving mechanism part 50 to move the optical length changing unit 40 in the direction of the optical axis, and thereby obtaining the two-dimensional tomographic image (B-scan image) of the fundus Ef. The obtained B-scan image is associated with the front image obtained precedently and is stored in the memory part 72.

Next, when the switch 73c is pressed, the calculation control part 70 controls to light the light source 22 to irradiate the stimulating light onto the fundus Ef. After the irradiation of the stimulating light, the calculation control part 70 controls the OCT optical system 100, the SLO optical system 200 and the image processing 71 to obtain the two-dimensional tomographic image (the B-scan image) of the fundus Ef and the front image of the fundus Ef after the irradiation of the stimulating light, which are stored in the memory part 72. The B-scan image after the irradiation of the stimulating light is obtained based on the information on the display position of the line 75 stored in the memory part 72.

When the images before/after the irradiation of the stimulating light are stored in the memory part 72 and the switch 73d is pressed, the image processing part 71, based on the tomographic images before/after the irradiation of the stimulating light stored in the memory part 72, measures the retinal function according to the difference of brightness (luminance) between the tomographic images to display a result of the measurement on the monitor 74.

Incidentally, in the above description, the measurement light is scanned by driving the scanning unit 20 based on the display position of the line 75 set on the front image; however, the present invention is not limited thereto. For example, it is also preferable that a measurement part having a housing in which the OCT optical system 100, the SLO optical system 200 and the like are housed, and a moving mechanism part which relatively moves the measurement part in the X- and Y-directions with respect to the eye E, are provided, and the measurement light is scanned by driving the moving mechanism part based on the display position of the line 75 set on the front image.

In addition, it is also preferable that a relative position of the OCT optical system 100 with respect to the eye E is detected based on the obtained front image, and the positional deviation between the tomographic images before/after the irradiation of the stimulating light is corrected by driving the moving mechanism part based on a detection result.

Incidentally, the three-dimensional images are also associated with the front images before/after the irradiation of the stimulating light to be stored, and the correction of the positional deviation is performed based on the front images. If the three-dimensional tomographic image has been obtained, the B-scan image and/or the C-scan image can be picked up, and the retinal function can be measured based on the picked-up images.

In addition, in the above description, as the OCT optical system 100, employed is a time domain OCT (TD-OCT) optical system in which the optical path length of the reference light is changed by the optical path length changing unit 40 to obtain an interference image; however, it is not limited thereto, and optical systems based on other principles may be employed. For example, employed may be a spectrum domain OCT (SD-OCT) optical system in which the interference light obtained by synthesizing the measurement light and the reference light is dispersed into frequency components via a diffraction grating to be photo-received on the photodetector, and the interference image is obtained by calculating the obtained photo-receiving signal using Fourier transform. As the OCT (so-called Fourier domain OCT) optical system in which the interference light is dispersed into the frequency components and photo-received for detecting spectral information of the interference light and obtaining the interference image using Fourier transform, employed may be a swept source OCT (SS-OCT) optical system in which the interference light is dispersed into the frequency components by using a wavelength variable light source (a frequency sweeping light source) which varies a wavelength of the measurement light in a time series to be photo-received on the photodetector, instead of employing the SD-OCT optical system.

Figure 5:
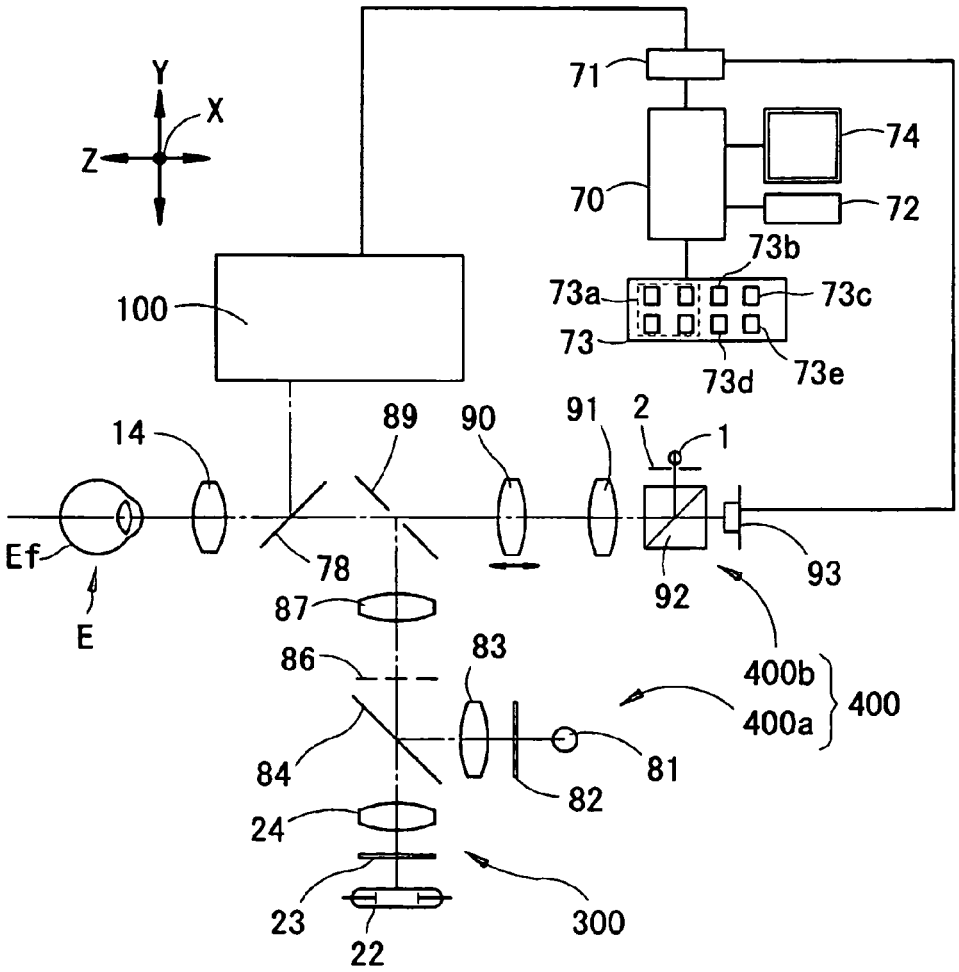
FIG. 5 is a view showing a schematic configuration of a modified embodiment of the optical system of the retinal function measurement apparatus.

Incidentally, in the above description, the relative positional deviation between the tomographic images before/after the irradiation of the stimulating light is corrected based on the front images before/after the irradiation of the stimulating light obtained by the SLO optical system 200; however, the present invention is not limited thereto. For example, the relative positional deviation between the tomographic images before/after the irradiation of the stimulating light may be corrected based on the front images before/after the irradiation of the stimulating light obtained by a fundus camera (FC) optical system. An example of such an embodiment will be described with reference to FIG. 5.

The FC optical system 400 includes an illumination optical system 400a and an image-pickup optical system 400b. The illumination optical system 400a includes a light source 81 such as a halogen light, a wavelength selecting filter 82 which filters out a range with wavelengths of 815 to 865 nm and transmits a range with wavelengths of 700 to 815 nm and a range with wavelengths of more than 865 nm, a condenser lens 83, a dichroic mirror 84 having properties of reflecting infrared light and transmitting visible light, a ring-slit plate 86, a relay lens 87, a hole mirror 89, and the objective lens 14. The ring-slit plate 86 and the hole mirror 89 are arranged in positions approximately conjugate with the pupil of the eye E. Light from the light source 81 is made into infrared light by the filter 82, which passes through the condenser lens 83, is reflected by the dichroic mirror 84, and is irradiated onto the fundus Ef via the ring-slit plate 86 to the objective lens 14.

The stimulating light irradiation optical system 300 includes the light source 22, the wavelength selecting filter 23, the projection lens 24, and the ring-slit plate 86 to the objective lens 14. Here, the light from the light source 22 passes through the wavelength selecting filter 23 and the projection lens 24, passes through the dichroic mirror 84, and is irradiated onto the fundus Ef via the same optical path as the light from the light source 81 (via the ring-slit plate 86 to the objective lens 14).

The image-pickup optical system 400b includes the objective lens 14, the hole mirror 89, a focusing lens 90 movable in the direction of the optical axis, an image forming lens 91, and a two-dimensional image-pickup element 93. The light from the light source 81 reflected from the fundus Ef passes through the objective lens 14, is once converged in front of the hole mirror 89 to pass through a hole thereof, passes through the focusing lens 90, is converged by the image forming lens 91, and forms an image on the image-forming element 93, thereby obtaining the front image of the fundus Ef.

The fixation target presenting optical system is made coaxial with the image-pickup optical system 400b by a dichroic mirror 92 having properties of reflecting visible light and transmitting infrared light.

Between the objective lens 14 and the hole mirror 89, arranged is a dichroic mirror 78 which makes the optical axis of the OCT optical system 100 coaxial with the optical axis of the stimulating light irradiation optical system 300 and the FC optical system 400. The dichroic mirror 78 has properties of reflecting the light from the light source 10 and transmitting the other light (the light from the light source 1, the light from the light source 22 (the filter 23), the light from the light source 82 (the filter 82)).

In this example also, the image processing part 71 obtains the front images by the image-pickup element 73 in accordance with timing of obtaining the tomographic images, and makes the memory part 72 store the images before/after the irradiation of the stimulating light. Concerning the subsequent calculating processing and the like such as the correction of the positional deviation, the description is omitted since it is the same as the already described one.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

[1. A retinal function measurement apparatus comprising:

a first image obtaining optical system that obtains a tomographic image of a fundus of an examiner's eye by optical coherence tomography using low coherent light, the first image obtaining optical system including a light source which emits the low coherent light, a scanning unit which scans measurement light being a part of the emitted low coherent light on the fundus, an interference optical system for synthesizing the measurement light reflected from the fundus and reference light being a part of the emitted low coherent light to interfere, and a first photodetector which photo-receives the interfered light;

a stimulating light irradiation optical system that performs irradiation of stimulating light, having a visible wavelength capable of stimulating a retina, onto the fundus;

a fixation target presenting optical system that performs fixation of the eye;

a memory that stores an obtained tomographic image;

a control unit that controls the first image obtaining optical system to obtain a first tomographic image of the fundus before the irradiation of the stimulating light onto the fundus and stores the first tomographic image in the memory, controls the stimulating light irradiation optical system to perform the irradiation of the stimulating light onto the fundus, controls the first image obtaining optical system to obtain a second tomographic image of the fundus after the irradiation of the stimulating light onto the fundus and stores the second tomographic image in the memory; and an image processing unit that obtains information on a retinal function by performing processing on the first tomographic image before the irradiation of the simulating light and the second tomographic image after the irradiation of the stimulating light, which are stored in the memory.]

[2. The retinal function measurement apparatus according to claim 1 further comprising a second image obtaining optical system for obtaining a front image of the fundus, and wherein the image processing unit calculates a relative positional deviation between a first front image obtained in obtaining the first tomographic image and a second front image obtained in obtaining the second tomographic image, and corrects a relative positional deviation between the first tomographic image and the second tomographic image based on the obtained positional deviation to perform the processing on both the tomographic images.]

[3. The retinal function measurement apparatus according to claim 2, wherein the second image obtaining optical system includes the light source and the scanning unit of the first image obtaining optical system, a confocal optical system with respect to the fundus, a beam splitter which divides the measurement light reflected from the fundus to guide the measurement light to the interference optical system and the confocal optical system, and a second photodetector which photo-receives the measurement light passed through the confocal optical system.]

[4. The retinal function measurement apparatus according to claim 2, wherein the second image obtaining optical system includes an illumination optical system, which shares a part of an optical path with the stimulating light irradiation optical system for performing irradiation of illumination light onto the fundus, and an image-pickup optical system for picking up the front image of the fundus by photo-receiving the illumination light reflected from the fundus.]

[5. The retinal function measurement apparatus according to claim 2 further comprising a setting unit which sets positional information for obtaining the tomographic image on the obtained front image, and wherein the first image obtaining optical system obtains the tomographic image based on the set positional information.]

[6. The retinal function measurement apparatus according to claim 1, wherein the first image obtaining optical system includes an optical path length changing unit which changes an optical path length of the reference light in synchronization with the scanning of the measurement light by the scanning unit.]

[7. The retinal function measurement apparatus according to claim 1, wherein the first image obtaining optical system includes a dispersing unit which disperses the interfered light into frequency components, and wherein the first photodetector photo-receives the dispersed light.]

[8. A retinal function measurement apparatus comprising:

a first image obtaining optical system that obtains a tomographic image of a fundus by optical coherence tomography using low coherent light, the first image obtaining optical system including a light source which emits the low coherent light, a scanning unit which scans measurement light being a part of the emitted low coherent light on the fundus, an interference optical system for synthesizing the measurement light reflected from the fundus and reference light being a part of the emitted low coherent light to interfere, and a first photodetector which photo-receives the interfered light;

a stimulating light irradiation optical system that performs irradiation of stimulating light onto the fundus;

an image processing unit that obtains information on a retinal function by performing processing on a first tomographic image before the irradiation of the stimulating light and a second tomographic image after the irradiation of the stimulating light; and a second image obtaining optical system that obtains a front image of the fundus, wherein the image processing unit calculates a relative positional deviation between a first front image obtained in obtaining the first tomographic image and a second front image obtained in obtaining the second tomographic image, and corrects a relative positional deviation between the first tomographic image and the second tomographic image based on the obtained positional deviation to perform the processing on both the tomographic images.]

[9. The retinal function measurement apparatus according to claim 8, wherein the second image obtaining optical system includes the light source and the scanning unit of the first image obtaining optical system, a confocal optical system with respect to the fundus, a beam splitter which divides the measurement light reflected from the fundus to guide the measurement light to the interference optical system and the confocal optical system, and a second photodetector which photo-receives the measurement light passed through the confocal optical system.]

[10. The retinal function measurement apparatus according to claim 8, wherein the second image obtaining optical system includes an illumination optical system, which shares a part of an optical path with the stimulating light irradiation optical system for performing irradiation of illumination light onto the fundus, and an image-pickup optical system for picking up the front image of the fundus by photo-receiving the illumination light reflected from the fundus.]

[11. The retinal function measurement apparatus according to claim 8, further comprising a setting unit which sets positional information for obtaining the tomographic image on the obtained front image, and wherein the first image obtaining optical system obtains the tomographic image based on the set positional information.]

*12. A method for comparing tomographic images of a same portion of a fundus that are obtained by an optical coherence tomography device, the method comprising:*

*obtaining a first three-dimensional tomographic image of the fundus by the optical coherence tomography device and a first front image of the fundus that is associated with the first three-dimensional tomographic image;*

*obtaining a second three-dimensional tomographic image of the fundus by the optical coherence tomography device at an interval from the obtainment of the first three-dimensional tomographic image and a second front image of the fundus that is associated with the second three-dimensional tomographic image;*

*performing alignment of the first front image and the second front image and associating the first three-dimensional tomographic image and the second three-dimensional tomographic image based on an alignment result; and*

*comparing the associated first and second three-dimensional tomographic images.*

*13. A method for comparing tomographic images of a same portion of a fundus that are obtained by an optical coherence tomography device, the method comprising:*

*obtaining a first tomographic image of the fundus by the optical coherence tomography device and a first front image of the fundus that is associated with the first tomographic image;*

*obtaining a second tomographic image of the fundus by the optical coherence tomography device at an interval from the obtainment of the first tomographic image and a second front image of the fundus that is associated with the second tomographic image,*

*wherein the obtainment of at least one of the first tomographic image and the second tomographic image by the optical coherence tomography device is performed by controlling driving of an optical scanner that is provided to the optical coherence tomography device based on information on an obtainment position of a fundus tomographic image with respect to a previously obtained fundus front image and a fundus front image that is obtained by a fundus observation optical system so that measurement light is scanned within a predetermined scanning range of the measurement light on the fundus; and*

*comparing the obtained first and second tomographic images.*

* * * * *